US012788836B2

(12) United States Patent
Chen et al.

(10) Patent No.: US 12,788,836 B2
(45) Date of Patent: Nov. 10, 2026

(54) LED PACKAGE STRUCTURE, AND DISINFECTION DEVICE AND DISINFECTION LAMP APPLYING SAME

(71) Applicants: Shanghai Sansi Electronic Engineering Co. Ltd., Shanghai (CN); Shanghai Sansi Technology Co. Ltd., Shanghai (CN); Jiashan Sansi Optoelectronic Technology Co. Ltd., Jiaxing (CN); Pujiang Sansi Optoelectronic Technology Co. Ltd., Jinhua (CN)

(72) Inventors: Bishou Chen, Shanghai (CN); Ming Chen, Shanghai (CN); Shan Li, Shanghai (CN); Xiaoliang He, Shanghai (CN)

(73) Assignees: Shanghai Sansi Electronic Engineering Co. Ltd., Shanghai (CN); Shanghai Sansi Technology Co. Ltd., Shanghai (CN); Jiashan Sansi Optoelectronic Technology Co. Ltd., Jiaxing (CN); Pujiang Sansi Optoelectronic Technology Co. Ltd., Jinhua (CN)

( * ) Notice: Subject to any disclaimer, the term of this patent is extended or adjusted under 35 U.S.C. 154(b) by 494 days.

(21) Appl. No.: 18/281,965

(22) PCT Filed: May 26, 2021

(86) PCT No.: PCT/CN2021/096092

§ 371 (c)(1),
(2) Date: Sep. 14, 2023

(87) PCT Pub. No.: WO2022/193435

PCT Pub. Date: Sep. 22, 2022

(65) Prior Publication Data

US 2024/0050612 A1 Feb. 15, 2024

(30) Foreign Application Priority Data

Mar. 15, 2021 (CN) ......................... 202110277321.6
Mar. 15, 2021 (CN) ......................... 202120534922.6

(51) Int. Cl.
*A61L 2/10* (2026.01)
*A61L 2/24* (2006.01)
(Continued)

(52) U.S. Cl.
CPC .................. *A61L 2/24* (2013.01); *A61L 2/10* (2013.01); *H10W 90/00* (2026.01);
(Continued)

(58) Field of Classification Search
CPC .......... A61L 2/10; A61L 2/24; A61L 2202/11; A61L 2202/14; H10W 90/00; G08B 21/24
See application file for complete search history.

(56) References Cited

U.S. PATENT DOCUMENTS 9,597,420 B2 * 3/2017 Maxik ....................... A61L 2/10
9,603,956 B2 * 3/2017 Newham ................. F21V 14/04
(Continued)

FOREIGN PATENT DOCUMENTS

CN 201935074 U 8/2011
CN 203363796 U 12/2013
(Continued)

*Primary Examiner* — Sean Luck

(57) ABSTRACT

An LED package structure, and a disinfection device and a disinfection lamp applying same. The LED package structure comprises: an LED wafer unit comprising a plurality of ultraviolet-band LED wafers and a visible light-band LED wafer. Each of the LED wafers is externally connected to a control unit for controlling whether each ultraviolet-band LED wafer emits light or not and a light emission intensity to emit light of different disinfecting bands and disinfecting effects as required, and controlling the visible light-band
(Continued)

LED wafer to emit illumination and/or warning light, thereby achieving a technical effect of multiple purposes in one lamp. Meanwhile, the present disclosure can meet various disinfection requirements by using one product structure, and therefore, compared with conventional single-function disinfection lamps, the present disclosure has a more compact structure to occupy a smaller space, and has an indication function to improve safety of ultraviolet disinfection.

8 Claims, 2 Drawing Sheets

(51) Int. Cl.
*H10W 90/00* (2026.01)
*G08B 21/24* (2006.01)

(52) U.S. Cl.
CPC ........ *A61L 2202/11* (2013.01); *A61L 2202/14* (2013.01); *G08B 21/24* (2013.01)

(56) References Cited

U.S. PATENT DOCUMENTS

| | | | | |
|---|---|---|---|---|
| 9,764,050 | B1 * | 9/2017 | Almeida | A61L 2/24 |
| 10,363,327 | B2 * | 7/2019 | Liao | H05B 45/10 |
| 10,413,623 | B2 * | 9/2019 | Bogdanovich | A61L 2/084 |
| 10,429,014 | B2 * | 10/2019 | Jenks | F21V 29/70 |
| 10,588,993 | B2 * | 3/2020 | Quilici | A61L 2/24 |
| 10,849,995 | B2 * | 12/2020 | Crosby | A61L 2/10 |
| 2007/0205382 | A1 * | 9/2007 | Gaska | A61L 2/10 250/492.1 |
| 2010/0181582 | A1 * | 7/2010 | Li | H10H 20/84 257/E33.056 |
| 2011/0243789 | A1 * | 10/2011 | Roberts | A61L 2/10 422/116 |
| 2012/0182755 | A1 * | 7/2012 | Wildner | F21S 4/20 362/555 |
| 2017/0254518 | A1 * | 9/2017 | Vasylyev | F21V 21/14 |
| 2018/0055959 | A1 * | 3/2018 | Lin | A61L 2/10 |
| 2018/0202618 | A1 * | 7/2018 | Jenks | G01N 21/91 |
| 2019/0038914 | A1 * | 2/2019 | Igarashi | A61N 5/0624 |
| 2019/0091358 | A1 * | 3/2019 | Liao | H05B 45/10 |
| 2019/0369298 | A1 * | 12/2019 | Ja | G02B 3/0068 |
| 2021/0338860 | A1 * | 11/2021 | Grenon | A61L 2/10 |

FOREIGN PATENT DOCUMENTS

| | | | |
|---|---|---|---|
| CN | 111271613 | A | 6/2020 |
| CN | 212322997 | U | 1/2021 |

* cited by examiner

LED PACKAGE STRUCTURE, AND DISINFECTION DEVICE AND DISINFECTION LAMP APPLYING SAME

TECHNICAL FIELD

The present disclosure relates to the field of LED package, in particular to an LED package structure, and a disinfection device and a disinfection lamp applying same.

BACKGROUND

Ultraviolet sterilization and disinfection mode has been widely recognized in the industry, but ultraviolet disinfection lamps often have a single band which cannot be adjusted, and following problems are easily encountered in actual use: (1) different germs need different bands of ultraviolet rays to kill; and (2) different items have different requirements for ultraviolet rays for sterilization and disinfection, for example, long wavelengths are needed for clothing for increased penetration.

Therefore, an ultraviolet disinfection lamp which can not only meet disinfection requirements of different germs, but also meet disinfection requirements of diversified items in life is urgently needed in this field.

SUMMARY

The present disclosure provides an LED package structure, including: an LED wafer unit including a plurality of ultraviolet-band LED wafers and a visible light-band LED wafer. Each of the LED wafers is externally connected to a control unit for the control unit to control whether each ultraviolet-band LED wafer emits light or not and a light emission intensity thereof to emit light of different disinfecting bands and disinfecting effects as required, and control the visible light-band LED wafer to emit illumination and/or warning light.

In some embodiments of the present disclosure, the LED package structure further includes: a support unit including a substrate and chip dams. The chip dams are arranged on the substrate and are used for dividing the substrate into a plurality of independent spaces for respectively holding the ultraviolet-band LED wafers and the visible light-band LED wafer.

In some embodiments of the present disclosure, the ultraviolet-band LED wafers include at least a UVA-band LED wafer, a UVB-band LED wafer and a UVC-band LED wafer; and the independent spaces divided by the chip dams respectively hold the UVA-band LED wafer, the UVB-band LED wafer, the UVC-band LED wafer and the visible light-band LED wafer.

In some embodiments of the present disclosure, each of the LED wafers is provided with a transparent filler, and the transparent filler is fixed on the substrate with a bonding material.

In some embodiments of the present disclosure, the bonding material is a moisture-proof and insulating material.

In some embodiments of the present disclosure, the transparent filler includes at least quartz glass, a lens, or transparent glue.

In some embodiments of the present disclosure, the support unit includes a plurality of strip-shaped chip dams arranged in a staggered manner for dividing the substrate into a plurality of independent spaces which are adjacent in pairs.

In some embodiments of the present disclosure, the support unit includes a plurality of annular chip dams arranged in a nested manner for dividing the substrate into a plurality of independent spaces which are nested annularly.

The present disclosure provides a disinfection device including: an LED package structure, including a plurality of ultraviolet-band LED wafers and a visible light-band LED wafer; and a control unit, electrically connected to the LED wafers of each band for the control unit to control whether each ultraviolet-band LED wafer emits light or not and a light emission intensity thereof to emit light of different disinfecting bands and disinfecting effects as required, and control the visible light-band LED wafer to emit illumination and/or warning light.

The present disclosure provides a disinfection lamp including the LED package structure.

As described above, the LED package structure, the disinfection device and the disinfection lamp applying the same provided in the present disclosure have following beneficial effects: the visible light-band LED wafer and the plurality of ultraviolet-band LED wafers are arranged; although different germs need different bands of ultraviolet rays to kill and different items have different requirements for ultraviolet rays for sterilization and disinfection, by controlling whether each ultraviolet-band LED wafer and the visible light-band LED wafer emit light or not and a light emission intensity to emit light of different disinfecting bands and disinfecting effects as required, and by controlling the visible light-band LED wafer to emit illumination and/or warning light, a technical effect of multiple purposes in one lamp is realized in the present disclosure. Meanwhile, the present disclosure can meet various disinfection requirements by using one product structure, and therefore, compared with conventional single-function disinfection lamps, the present disclosure has a more compact structure to occupy a smaller space, and has an indication function to improve safety of ultraviolet disinfection.

DETAILED DESCRIPTION

Figure 1:
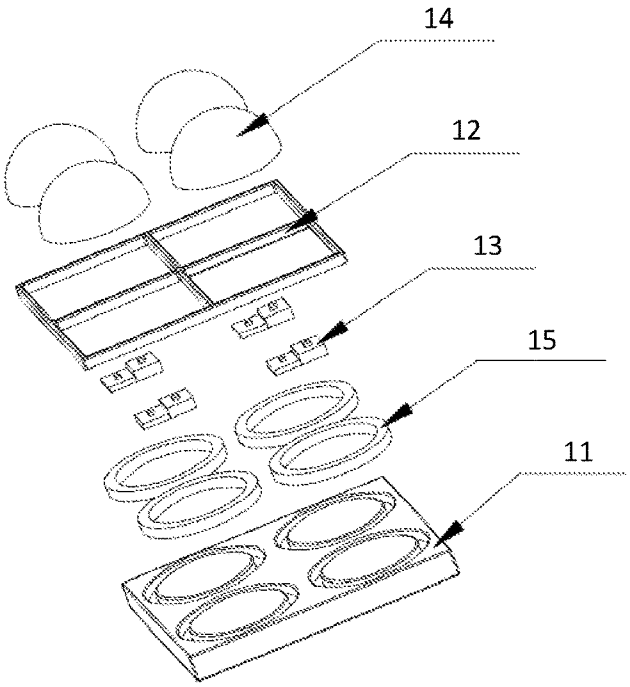
FIG. 1 is an exploded view of an LED package structure according to an embodiment of the present disclosure.

Implementation modes of the present disclosure will be described hereinafter with reference to specific embodiments, and additional advantages and benefits of the present disclosure are readily apparent to those skilled in the art from the disclosure herein.

It is to be understood that structures, proportions, and sizes shown in drawings of this description are only used for matching a content disclosed in the description for those skilled in the art to understand and read, and are not intended to limit limiting conditions under which the present disclosure can be implemented, and therefore do not have any technical substantive meaning. Any structure modification, proportion relationship change, or size adjustment, without affecting generated efficacy and achieved purposes of the present disclosure, still falls in a scope of the technical content disclosed by the present disclosure. Following detailed description is not to be taken in a limiting sense, and a scope of embodiments of the present application is defined only by claims of an issued patent. Terms used herein are used for describing specific embodiments only and are not intended to limit the present application. Spatially relevant terms such as "up", "down", "left", "right", "under", "below", "lower", "above", "upper" and the like may be used herein to facilitate describing a relationship of one element or feature to another element or feature shown in a drawing.

In the present disclosure, unless otherwise clearly specified and limited, terms "arrangement", "link", "connection", "fixing" and "holding" are widely understood, for example, fixed connection, detachable connection and integrated connection are all possible; both mechanical connection and electric connection are possible; and direct connection, indirect connection through an intermedium, and an internal communication between two elements are possible. Those skilled in the art can understand specific meanings of the above terms in the present disclosure according to a specific situation.

Furthermore, as used herein, singular forms "a", "an" and "the" are intended to include plural forms as well, unless the context indicates otherwise. It should be further understood that terms "comprise" and "include" specify presence of the features, operations, elements, components, items, categories, and/or groups, but do not preclude presence, occurrence, or addition of one or more other features, operations, elements, components, items, categories, and/or groups. Terms "or" and "and/or" as used herein are to be construed as inclusive, or to mean any one or any combination. Thus, "A, B or C" or "A, B and/or C" means "any of the following: A; B; C; A and B; A and C; B and C; A, B, and C". An exception of the definition appears when a combination of elements, functions, or operations is inherently mutually exclusive in a certain way.

The present disclosure provides an LED package structure, and a disinfection device and a disinfection lamp applying same. UVA, UVB, UVC and visible light wafers are packaged together, each wafer is respectively connected to a control part, and presence and a size of light of each band are controlled by adjusting a magnitude of current. The LED package structure can be applied to LED disinfection equipment so as to realize disinfection of different bands and functions of visible light illumination and indication. In order to make purposes, technical solutions and advantages of the present disclosure more clearly understood, the technical solutions in the embodiments of the present disclosure are further described in detail through the following embodiments and in conjunction with the drawings. It should be understood that the specific embodiments described herein are merely illustrative of the present disclosure and are not intended to limit the present disclosure.

Embodiment 1

The present disclosure provides an LED package structure, including an LED wafer unit. The LED wafer unit includes a plurality of ultraviolet-band LED wafers and a visible light-band LED wafer. Each of the LED wafers is externally connected to a control unit for the control unit to control whether each ultraviolet-band LED wafer emits light or not and a light emission intensity of each ultraviolet-band LED wafer, to emit light of different disinfecting bands and disinfecting effects as required, and control the visible light-band LED wafer to emit illumination and/or warning light.

For example, at night when there is no disinfection requirement, the control unit can control to activate the visible light-band LED wafer to emit illumination light; under a condition of specific disinfection requirements, the control unit can control an LED wafer of a corresponding band to emit light of a corresponding disinfecting band and disinfecting effects, can adjust penetration of the light of the band by adjusting a light emission intensity, and when the ultraviolet-band LED wafers are on, can control the visible-band LED wafer to alert the surrounding population to stay away by warning light such as flash and/or color change.

In some examples, the LED package structure further includes a support unit. The support unit includes a substrate and chip dams, the chip dams are arranged on the substrate and are used for dividing the substrate into a plurality of independent spaces for respectively holding the ultraviolet-band LED wafers and the visible light-band LED wafer.

It should be noted that the control unit may be specifically an ARM (Advanced RISC Machines) controller, an FPGA (Field Programmable Gate Array) controller, an SoC (System on Chip) controller, a DSP (Digital Signal Processing) controller, or an MCU (Microcontroller Unit) controller. In addition, it is worth noting that the LED package structure provided in this embodiment can be applied to fields of LED disinfection, LED illumination and the like, and of course, it can also be applied to a field of display screens, which is not limited by this embodiment.

For ease of understanding, detailed description is made in conjunction with an exploded view of an LED package structure shown in FIG. 1. A substrate 11 is provided with chip dams 12, the chip dams 12 divide the substrate 11 into a plurality of independent spaces, and each independent space respectively holds each of the LED wafers 13, so as to play a role of isolating fluorescent powder.

The substrate 11 is mainly used for supporting each individual LED wafer, providing insulation and good heat conduction when the LED wafer is power-on. Different LED wafers are independently powered through respective positive polarity and negative polarity, independently conducted, independently work according to magnitudes of control voltage and current, and independently emit different UV-band light or visible light. Through different combinations of conduction control and different durations of conduction, light of different disinfecting bands and disinfecting effects can be emitted as required; and after the visible light-band LED wafer is conducted, illumination light or warning light can be emitted.

In this embodiment, the LED wafers 13 include the ultraviolet-band LED wafers and the visible light-band LED wafer. The ultraviolet-band LED wafers include at least a UVA-band LED wafer, a UVB-band LED wafer and a UVC-band LED wafer. Therefore, the chip dams 12 divide the substrate 11 into four independent spaces for respectively holding the UVA-band LED wafer, the UVB-band LED wafer, the UVC-band LED wafer and the visible light-band LED wafer.

It should be understood that the above UVA-band LED wafer, the UVB-band LED wafer, and the UVC-band LED wafer are classified according to wavelengths of ultraviolet bands, and description of each ultraviolet band and the visible light band is as follows:

the UVA band refers to ultraviolet A with a black spot effect and a wavelength ranges from 400 nm to 320 nm (long wave). The UVA has strong penetration and can penetrate most transparent glass and plastics. More than 98% of UVA contained in sunlight can penetrate an ozone layer and clouds to reach the earth's surface, directly reach dermis of a skin, destroy elastic fibers and collagen fibers, and tan the skin; UVA with a wavelength of 360 nm conforms to a phototaxis reaction curve of insects, and can be used to make a trap lamp.

The UVB band refers to ultraviolet B with an erythema effect and a wavelength ranges from 320 nm to 275 nm (medium wave). The UVB has medium penetration, and its shorter wavelength part may be absorbed by transparent glass. Most UVB contained in sunlight can be absorbed by the ozone layer, and only less than 2% can reach the earth's surface. It may be particularly strong in summer and afternoon. UVB ultraviolet rays have an erythema effect on a human body, and can promote metabolism of minerals and formation of vitamin D in the body. An ultraviolet health care lamp and a plant growth lamp are made of special uviol glass and fluorescent powder with a peak value near 300 nm.

The UVC band refers to sterile ultraviolet with a wavelength ranges from 275 nm to 200 nm (short wave). The UVC has the weakest penetration and cannot penetrate most transparent glass and plastics. UVC contained in sunlight is almost completely absorbed by the ozone layer. The UVC causes great harm to the human body and can burn the skin under short-time exposure. Ultraviolet rays emitted for disinfection are UVC.

The visible light band is a part of an electromagnetic spectrum which can be perceived by human eyes. Generally, a wavelength of electromagnetic waves which can be perceived by human eyes is between 780 and 400 nm, and the visible light is composed of seven colors of light, such as red, orange, yellow, green, blue, indigo and purple. Commonly used visible light lamps are incandescent lamps, halogen lamps, fluorescent lamps, energy-saving lamps, LED lamps, high-pressure sodium lamps, neon lamps and so on.

In this embodiment, one or more of the UVA-band LED wafer, the UVB-band LED wafer, the UVC-band LED wafer, and the visible light-band LED wafer may be combined as required, and the visible light may be used for indication or illumination, and the ultraviolet light may be used for disinfection. A preferred combination is: the visible light-band LED wafer and one of the ultraviolet-band LED wafers, namely the visible light-band LED wafer+the UVA-band LED wafer/the UVB-band LED wafer/the UVC-band LED wafer; or the visible-band LED wafer and two of the ultraviolet-band LED wafers, namely, the visible-band LED wafer+(the UVA-band LED wafer+the UVB-band LED wafer)/(the UVA-band LED wafer+the UVC-band LED wafer)/(the UVB-band LED wafer+the UVC-band LED wafer); or, the visible-band LED wafer and the three ultraviolet-band LED wafers, namely, the visible-band LED wafer+the UVA-band LED wafer+the UVB-band LED wafer+the UVC-band LED wafer. The visible light band includes white light, red light, blue light, green light, and the like, and can be used for an indication lamp or an illumination lamp.

It should also be noted that the above examples are only for reference and do not limit the scope of the present disclosure, and the present disclosure does not limit the number of ultraviolet-band LED wafers.

In some examples, each of the LED wafers 13 is provided with a transparent filler 14, and the transparent filler 14 is fixed on the substrate 11 with a bonding material 15. The substrate 11 may be specifically a ceramic substrate, a metal substrate (such as an aluminum substrate or a copper substrate), or an organic substrate.

Furthermore, the bonding material is a moisture-proof and insulating material, or moisture-proof insulating paint is applied to the surface of the bonding material. The transparent filler may be quartz glass, a lens, or a transparent material (such as glue). In the above scheme, the number of LED wafers in each independent space is not limited, and the LED wafers can be attached to the substrate or fixed on the substrate in other ways.

Figure 2A:
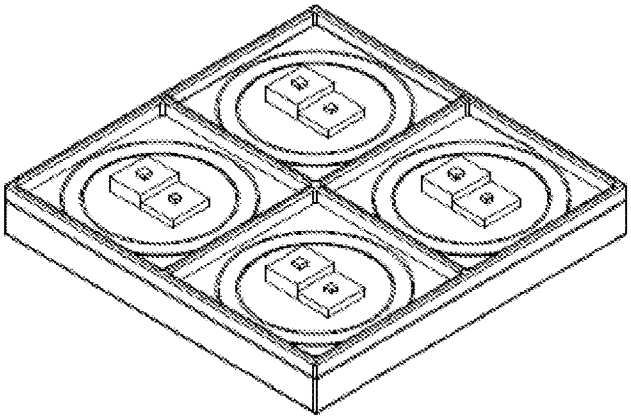
FIG. 2A is a schematic view of an LED package structure without a transparent filling material according to an embodiment of the present disclosure.
Figure 2B:
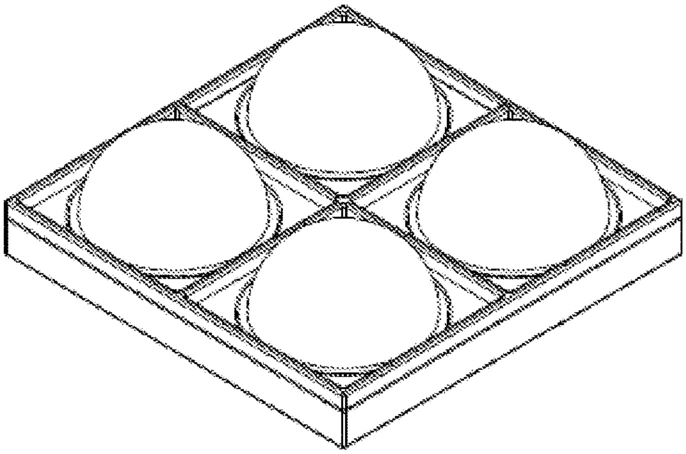
FIG. 2B is a schematic view of an LED package structure with a transparent filling material according to an embodiment of the present disclosure.

Corresponding to the exploded view of the LED package structure shown in FIG. 1, FIGS. 2A and 2B respectively show assembling schematic views of the LED package structure. FIG. 2A is the schematic view of the LED package structure without a transparent filling material, and FIG. 2B is the schematic view of the LED package structure with a transparent filling material. After the LED package structure is assembled, the power-on method may be a conductive connection, preferably a gold wire connection with high conductivity, corrosion resistance, and excellent toughness, or a circuit board connection.

Figure 3A:
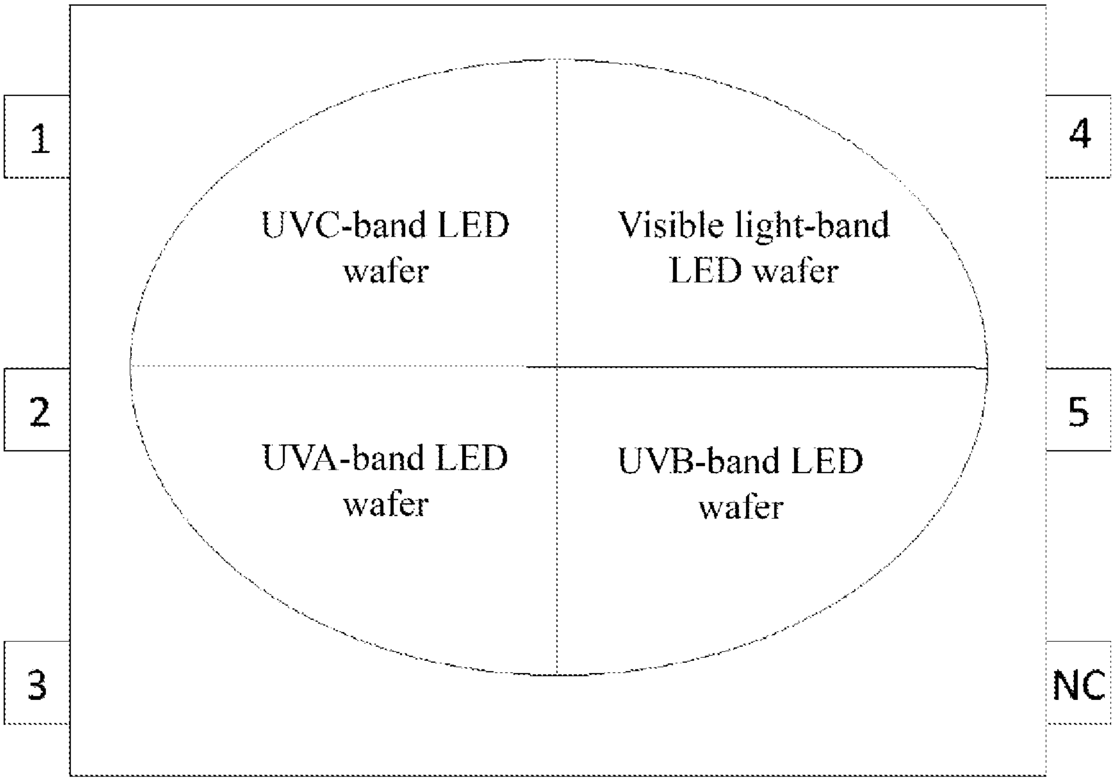
FIG. 3A is a schematic view of an LED wafer arrangement mode according to an embodiment of the present disclosure.

In some examples, the support unit includes a plurality of strip-shaped chip dams arranged in a staggered manner for dividing the substrate into a plurality of independent spaces which are adjacent in pairs. For example, as shown in FIG. 3A, the chip dams divide the substrate into four independent spaces which are adjacent in pairs, and the independent spaces respectively hold a visible light-band LED wafer, a UVA-band LED wafer, a UVB-band LED wafer, and a UVC-band LED wafer.

Figure 3B:
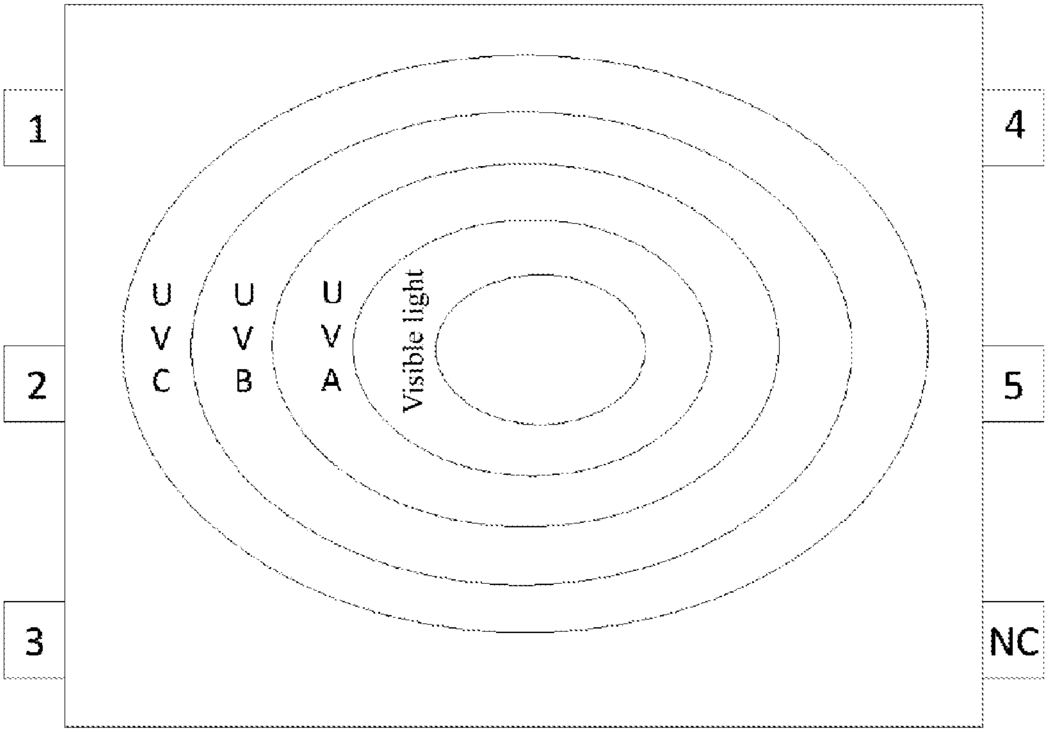
FIG. 3B is a schematic view of an LED wafer arrangement mode according to an embodiment of the present disclosure.

In some examples, the support unit includes a plurality of annular chip dams arranged in a nested manner for dividing the substrate into a plurality of independent spaces which are nested annularly. For example, as shown in FIG. 3B, the chip dams divide the substrate into four independent spaces which are nested annularly, and the independent spaces respectively hold a visible light-band LED wafer, a UVA-band LED wafer, a UVB-band LED wafer, and a UVC-band LED wafer.

To sum up, although different germs need different bands of ultraviolet rays to kill and different articles require different ultraviolet rays for sterilization and disinfection, the LED package structure in this embodiment can emit light of different disinfecting bands and disinfecting effects as required by controlling whether each ultraviolet-band LED wafer emits light or not and a light emission intensity, and emit illumination and/or warning light by controlling the visible light-band LED wafer, and a technical effect of multiple purposes in one lamp is realized.

Embodiment 2

This embodiment provides an LED disinfection device, including an LED package structure and a control unit, wherein the LED package structure includes a plurality of ultraviolet-band LED wafers and a visible light-band LED wafer; and the control unit is electrically connected to the LED wafers of each band for the control unit to control whether each ultraviolet-band LED wafer emits light or not and a light emission intensity of each ultraviolet-band LED, to emit light of different disinfecting bands and disinfecting effects as required, and control the visible light-band LED wafer to emit illumination and/or warning light.

The LED disinfection device provided in this embodiment may be specifically an LED lamp or an LED display screen, which is not limited in this embodiment. It should also be noted that the LED package structure has been explained in detail in the above embodiment, and thus this embodiment omits the description. The control unit may be specifically an ARM (Advanced RISC Machines) controller, an FPGA (Field Programmable Gate Array) controller, an SoC (System on Chip) controller, a DSP (Digital Signal Processing) controller, or an MCU (Microcontroller Unit) controller.

Embodiment 3

This embodiment provides a disinfection lamp, including the above LED package structure. The LED package structure has been explained in detail in the above embodiment, and thus this embodiment omits the description.

It should be understood that ultraviolet disinfection is based on a principle of radiation, which can transmit electromagnetic wave energy penetrating through air and space at a speed of light. A working principle of the ultraviolet disinfection lamp is that a lamp tube is made of quartz glass with a high ultraviolet penetration rate as a protective outer tube, and when nucleic acids absorb ultraviolet rays with an artificial wavelength of 254 nm from a low-pressure mercury discharge lamp at a great absorption value, a genetic material of life from bacteria and viruses is destroyed, and intense chemical change is generated within molecules to prevent reproduction.

In summary, according to the LED package structure, and the disinfection device and the disinfection lamp applying the same provided by the present disclosure, the visible light-band LED wafer and a plurality of ultraviolet-band LED wafers are arranged. Although different germs need different bands of ultraviolet rays to kill and different items have different requirements for ultraviolet rays for sterilization and disinfection, by controlling whether each ultraviolet-band LED wafer and the visible light-band LED wafer emit light or not and a light emission intensity thereof to emit light of different disinfecting bands and disinfecting effects as required, and by controlling the visible light-band LED wafer to emit illumination and/or warning light, a technical effect of multiple purposes in one lamp is realized in the present disclosure. Meanwhile, the present disclosure can meet various disinfection requirements by using one product structure, and therefore, compared with conventional single-function disinfection lamps, the present disclosure has a more compact structure and occupies a smaller space, and has an indication function to improve safety of ultraviolet disinfection. Therefore, the present disclosure effectively overcomes various defects in the prior art and has a high industrial utilization value.

The above embodiments are merely illustrative of principles of the present disclosure and its utility, and are not intended to limit the present disclosure. Any person skilled in the art can modify or change the above embodiments without departing from the spirit and scope of the present disclosure. Accordingly, it is intended that all such equivalent modifications or variations made by persons skilled in the art without departing from the spirit and scope of the present disclosure shall be covered by the claims of the present disclosure.

What is claimed is:

1. An LED package structure, comprising:

an LED chip unit, comprising LED chips which comprise a plurality of ultraviolet-band LED chips and a visible light-band LED chip, and a support unit comprising a substrate configured to support the LED chip unit and chip dams disposed on the substrate, wherein each of the LED chips is operatively connected to an external control unit, such that the control unit controls whether each of the plurality of ultraviolet-band LED chips emits light or not and a light emission intensity thereof, to emit light of different disinfecting bands and disinfecting effects as required, and controls the visible light-band LED chip to emit illumination and/or warning light, wherein the chip dams partition the substrate into a plurality of independent spaces, and each of the plurality of independent spaces accommodates the LED chips of a respective wavelength band, wherein each of the plurality of independent spaces is provided with a transparent filler, the transparent filler being fixed to the substrate by a bonding material, wherein the transparent fillers of the plurality of independent spaces comprise at least one of quartz glass and lenses.

2. The LED package structure according to claim 1, wherein the plurality of ultraviolet-band LED chips comprise one or more of a UVA-band LED chip, a UVB-band LED chip and a UVC-band LED chip.

3. The LED package structure according to claim 1, wherein the bonding material is a moisture-proof and insulating material.

4. The LED package structure according to claim 1, wherein the chip dams are strip-shaped and arranged in a staggered manner, partitioning the substrate into the plurality of independent spaces which are adjacent in pairs.

5. The LED package structure according to claim 1, wherein the chip dams are annular and arranged in a nested manner, partitioning the substrate into the plurality of independent spaces which are nested annularly, wherein the visible light-band LED chip is disposed in an innermost one of the plurality of independent spaces.

6. An LED disinfection device, comprising:

an LED package structure, comprising an LED chip unit and a support unit comprising a substrate configured to support the LED chip unit and chip dams disposed on the substrate, wherein the LED chip unit comprises a plurality of ultraviolet-band LED chips and a visible light-band LED chip, wherein the chip dams partition the substrate into a plurality of independent spaces, and each of the plurality of independent spaces accommodates the LED chips of a respective wavelength band, wherein each of the plurality of independent spaces is provided with a transparent filler, the transparent filler being fixed to the substrate by a bonding material, wherein the transparent fillers of the plurality of independent spaces comprise at least one of quartz glass and lenses; and a control unit, electrically connected to the LED wafers, such that the control unit controls whether each of the plurality of ultraviolet-band LED chips emits light or not and a light emission intensity thereof, to emit light of different disinfecting bands and disinfecting effects as required, and controls the visible light-band LED chip to emit illumination and/or warning light.

7. VA disinfection lamp, comprising the LED package structure according to claim 1.

8. The LED package structure according to claim 1, wherein, upon one of the plurality of ultraviolet-band LED chips being turned on, the control unit controls the visible-light-band LED chip to emit a warning light.

* * * * *